United States Patent [19]
Jampani et al.

[11] Patent Number: 6,022,551
[45] Date of Patent: Feb. 8, 2000

[54] ANTIMICROBIAL COMPOSITION

[75] Inventors: Hanuman B. Jampani, Grapevine; Jerry L. Newman, Arlington, both of Tex.

[73] Assignee: Ethicon, Inc., Somerville, N.J.

[21] Appl. No.: 09/009,596

[22] Filed: Jan. 20, 1998

[51] Int. Cl.[7] .............................. A01N 25/00; A61K 7/00; A61K 31/44; A61K 31/14; A61K 31/045
[52] U.S. Cl. ..................... 424/405; 424/401; 514/358; 514/642; 514/724; 514/758
[58] Field of Search ..................... 424/401, 405; 514/642, 758, 358, 724

[56] References Cited

U.S. PATENT DOCUMENTS

| | | |
|---|---|---|
| 2,798,053 | 7/1957 | Brown . |
| 3,133,865 | 5/1964 | Richardson et al. . |
| 3,886,277 | 5/1975 | Randebrock et al. . |
| 4,134,412 | 1/1979 | Gross et al. . |
| 4,202,881 | 5/1980 | Gross et al. . |
| 4,257,907 | 3/1981 | Langguth et al. . |
| 4,268,424 | 5/1981 | Hall et al. . |
| 4,303,543 | 12/1981 | Mansy . |
| 4,326,997 | 4/1982 | Willis et al. . |
| 4,423,041 | 12/1983 | Clum et al. ............... 424/184 |
| 4,426,310 | 1/1984 | Verunica . |
| 4,464,293 | 8/1984 | Dobrin . |
| 4,474,807 | 10/1984 | Gerhardt et al. . |
| 4,668,513 | 5/1987 | Reichert ................... 424/94.6 |
| 4,690,821 | 9/1987 | Smith et al. . |
| 4,804,750 | 2/1989 | Nishimura et al. . |
| 4,816,451 | 3/1989 | Schriewer et al. . |
| 4,849,455 | 7/1989 | Eggers et al. . |
| 4,923,862 | 5/1990 | Hirota . |
| 4,956,170 | 9/1990 | Lee . |
| 4,957,908 | 9/1990 | Nelson . |
| 4,966,754 | 10/1990 | Purohit et al. ............... 424/195.1 |
| 5,004,598 | 4/1991 | Lochead et al. . |
| 5,053,407 | 10/1991 | Hayakawa et al. . |
| 5,098,717 | 3/1992 | Blackman . |
| 5,100,672 | 3/1992 | Gueret et al. ............... 424/449 |
| 5,109,019 | 4/1992 | Lehmann et al. . |
| 5,164,107 | 11/1992 | Khan et al. . |
| 5,180,061 | 1/1993 | Khan et al. . |
| 5,180,749 | 1/1993 | Cusak et al. . |
| 5,188,756 | 2/1993 | Baker et al. ............... 252/174.15 |
| 5,236,699 | 8/1993 | Libin ............... 424/54 |
| 5,288,486 | 2/1994 | White . |
| 5,308,890 | 5/1994 | Snyder . |
| 5,326,492 | 7/1994 | Hodam, Jr. . |
| 5,335,373 | 8/1994 | Dangman et al. . |
| 5,336,305 | 8/1994 | Staats . |
| 5,401,741 | 3/1995 | Saro et al. . |
| 5,403,587 | 4/1995 | McCue et al. ............... 424/195.1 |
| 5,403,864 | 4/1995 | Bruch et al. ............... 514/721 |
| 5,416,109 | 5/1995 | Donofrio et al. . |
| 5,420,104 | 5/1995 | Holzner et al. . |
| 5,512,199 | 4/1996 | Khan et al. . |
| 5,540,853 | 7/1996 | Trinh et al. . |
| 5,567,428 | 10/1996 | Hughes ............... 424/401 |
| 5,607,681 | 3/1997 | Galley et al. . |
| 5,626,837 | 5/1997 | Shimada et al. . |
| 5,661,170 | 8/1997 | Chodosh ............... 514/390 |
| 5,665,742 | 9/1997 | Mori et al. . |
| 5,681,802 | 10/1997 | Fujiwara et al. ............... 510/130 |
| 5,683,683 | 11/1997 | Scafidi ............... 424/70.19 |
| 5,709,872 | 1/1998 | Rees ............... 424/420 |
| 5,725,845 | 3/1998 | Krog et al. ............... 424/64 |

FOREIGN PATENT DOCUMENTS

| | | |
|---|---|---|
| 600269 | 5/1987 | Australia . |
| 2 326 167 | 12/1998 | Germany . |
| WO 94/27436 | 12/1994 | WIPO . |

OTHER PUBLICATIONS

Lee W. Bush, Leslee M. Benson, and John H. White, Pig Skin Test Subtrate for Evaluating Topical Antimicrobial Activity, Sep. 1986, Journal of Clinical Microbiology.

Chemical Abstracts, Jones, M.N. et al.: "The Use of Phospholipid Liposomes for Targeting to Oral and Skin–Associated Bacteria" vol. 122, No. 8, Feb. 20, 1995, Abstract No. 89251, XP002102019.

*Primary Examiner*—Shelley A. Dodson
*Assistant Examiner*—Marina Lamm
*Attorney, Agent, or Firm*—Joseph F. Leightner

[57] ABSTRACT

A rapidly acting antimicrobial alcohol-containing composition and method of using the composition to disinfect surfaces, such as the hands is disclosed.

20 Claims, No Drawings

ANTIMICROBIAL COMPOSITION

This application is related to my U.S. patent applications, Ser. Nos. 09/009,091, entitled ALCOHOL BASED ANTIMICROBIAL COMPOSITION WITH COSMETIC APPEARANCE; and 09/009,489, entitled LOW TACK LOTION, GELS AND CREAMS, all concurrently filed herewith and which are assigned to assignee of the present invention and incorporated by reference as if fully set forth herein.

The present invention relates antimicrobial compositions which are topically applied to a substrate, such as the hands.

BACKGROUND OF THE INVENTION

Alcohol-containing antimicrobial compositions have been used in the healthcare industry for many years. More recently, alcohol and chlorhexidine gluconate compositions have been developed due to their long lasting efficacy and rapid kill of microorganisms. However, recent emergence of resistant microorganisms to antibiotic drugs and multi-drug resistance to a number of other antibiotics restricted the use of topical products containing antibiotics. Hospital staffs are seeking multifunctional products which meet their needs in terms of safety and performance against these emerging organisms. It would also be highly desirable to be able to provide this antimicrobial composition in a convenient dosage form for the hospital environment.

One attempt at solving this problem is the use of multiple antimicrobial compositions as disclosed in U.S. Pat. No. 5,403,864. This patent discloses an alcohol based solution which contains antimicrobial compounds, triclosan and chloroxylenol.

In addition to hospital and healthcare environments, awareness among consumers regarding antimicrobial compounds are increasing, and the desire for safe, mild and effective compositions for the home are also necessary. Preferably the antimicrobial compositions will solve these problems while remaining non-drying or preferably providing moisture that reduces the irritation levels associated with present antimicrobial compositions.

Accordingly, there is a continuing desire for an antimicrobial composition that is effective while also being non-irritating to users.

SUMMARY OF THE INVENTION

One embodiment of the present invention provides an antimicrobial composition comprising of a) an antimicrobial selected from the group consisting of more than 30% by volume alcohol and an effective amount of triclosan; and b) an effective amount of phenoxy ethanol, an effective amount of benzalkonium chloride or benzethonium chloride; and an effective amount of PHOSPOLIPID CDM.

In a second embodiment of the invention the antimicrobials are provided with an effective amount of triclosan, GERMALL PLUS and GERMABEN II. Additionally, the antimicrobial composition optionally also contains an effective amount of PHOSPOLIPID PTC.

In yet another embodiment of the present invention, the antimicrobial compositions also demonstrated surprising bactericidal activity against Staphyloccus aureaus (MRSA). The present invention also demonstrated excellent bactericidal activity against Serratia marcescens ATCC 14756 which has demonstrated weak susceptibility to triclosan-based formulations.

DETAILED DESCRIPTION OF THE INVENTION

The alcohol content of the present invention is greater than about 30 percent by volume, typically from about 55 to about 90 percent by volume, preferably from 60 to about 85 and most preferably from 60 to about 70% by volume of the composition. The alcohols useful in the present invention include, ethyl alcohol, iso-propyl alcohol, n-propyl alcohol and combinations thereof. Ethyl alcohol may be used as the only alcohol in the invention or in another embodiment the alcohol content in the invention provides ethyl alcohol from about 40 to about 70% by volume, iso-propyl alcohol from about 5 to about 25% by volume and n-propyl alcohol from about 5 to about 25% by volume.

Triclosan is employed from about 0.1 to about 0.5, preferably from about 0.2 to about 0.4 by weight.

The present invention contains a mixture of an effective amount of antimicrobials phenoxy ethyl alcohol, PHOSPHOLIPID CDM, benzalkonium chloride, and preferably GERMALL PLUS and GERMABEN II. Phenoxy ethanol is used from about 0.25 to about 5.0 percent by weight, preferably from about 0.3 to about 0.7, most preferably at about 0.05 percent by weight. PHOSPHOLIPID CDM is used from about 0.01 to about 1.0, preferably from about 0.03 to about 0.7, most preferably 0.5 percent by weight. Benzethonium chloride or preferably benzalkonium chloride is used from about 0.02 to about 1.0, preferably from about 0.08 to about 0.5, most preferably about 0.1 to about 0.2 percent by weight.

Other antimicrobial compositions have been found to particularly effective in improving the efficacy of the invention. These compositions include triclosan, PHOSPHOLIPID PTC, GERMALL PLUS and GERMABEN II.

The amount of GERMALL PLUS and GERMABEN II, independently provided in the invention varies from about 0.05 to about 0.5 with 0.1 percent by weight preferred. In the present invention the use of GERMALL PLUS and GERMABEN II together has been found to be highly effective. The ratio of the two materials when employed together is from about 0.1:1 to 1:0.1 and most preferably 1:1 weight ratio.

In addition to the antimicrobial compositions recited above, other antimicrobials may be employed with the present invention including nisin, bis-guanides, chlorhexidine gluconate, chlorhexidine digluconate, chlorhexidine diacetate, chlorhexidine dihydrochlorider tricloban, sodium hydroxy methyl glycinate, octanoyl collagenic acid, cetyl pyridium chloride, phenol, iodine, parachlorometaxylenol (PCMX), polymeric quaternary ammonium compounds, their combinations and the like. The antimicrobial compositions are typically added at a level of from 0.1 to about 4.0 percent by weight.

Other preferred ingredients employed in the invention include PHOSPOLIPID PTC, which is employed from about 0.01 to about 1.0, preferably from about 0.02 to about 0.08, and most preferably about 0.05 percent by weight. Australian tea tree oil and lemon grass oil are used in 1:1 ratio from about 0.5 to about 10.0, preferably from about 1.0 to about 7.0, and most preferably 5.0 weight percent.

One highly preferred embodiment of the invention provides more than 40% by weight alcohol, an effective amount of phenoxy ethanol, an effective amount of benzalkonium chloride, an effective amount of GERMALL PLUS, an effective amount of GERMABEN-II, and an effective amount of PHOSPOLIPID CDM. Additionally, the antimicrobial composition optionally also contains an effective amount of PHOSPOLIPID PTC.

In another preferred embodiment the antimicrobial mixture comprises greater than about 40% by weight alcohol, an effective amount of phenoxy ethanol, an effective amount of benzalkonium chloride, an effective amount of triclosan, an effective amount of GERMALL Plus, an effective amount of GERMABEN-II, and an effective amount of PHOSPO-LIPID CDM.

In yet another preferred embodiment of the invention the antimicrobial mixture contains greater than about 40% by weight alcohol, an effective amount of phenoxy ethanol, an effective amount of benzalkonium chloride, an effective amount of benzethonium chloride, an effective amount of triclosan, an effective amount of GERMALL Plus, an effective amount of GERMABEN-II, and an effective amount of PHOSPOLIPID CDM.

In another highly preferred embodiment of the invention the antimicrobial mixture is greater than 40% by weight a mixture of alcohols such as ethyl alcohol, iso-propyl alcohol, and n-propyl alcohol, a mixture of two essential oils such as Australian tea tree oil, and lemon grass oil, an effective amount of phenoxy ethanol, an effective amount of benzalkonium chloride, an effective amount of triclosan, an effective amount of GERMALL plus, an effective amount of GERMABEN-II, and an effective amount of PHOSPO-LIPID CDM. Additionally, the antimicrobial composition optionally also contains an effective amount of Vitamin E linoleate.

The antimicrobial compositions of the present invention are found to possess immediate and persistent activity over time. The compositions of the present invention also compare favorably with antimicrobial compositions which contain high levels of chlorhexidine gluconate or commercial products such as HIBISTAT and HIBICLENS, available from ZENECA Pharmaceuticals, which are commonly being used for disinfecting surgical scrubs, hand disinfectants and in preoperative preparation of patients.

It is known in the art that chlorohexidine gluconate formulations exhibit a great build-up in activity between washes 1 and 7. This increase in activity is believed to be caused by its polar structure and its ability to attach to skin. After ten washes and neutralization with suitable inactivator, the activity of chlorhexidine gluconate falls significantly (approximately 30–50%) at wash 10, when testing is performed in accordance with a Health Care personel hand wash protocol. Surprisingly, the compositions of the present invention provide more persistent antimicrobial activity than these other well-known antimicrobial agents.

Another advantage of the present invention is the residual activity provided by the antimicrobial product. The present invention provides effective protection against a broad spectrum of organisms, including gram positive, gram negative, yeast and fungi both at the initial application time, but also after an extended period of time. We have found that unike other antimicrobial compositions which are initially effective in killing microbes but which quickly lose their efficacy in about one hour. Surprisingly, the present invention is effective in preventing the appearance of microbes for an extended periods of time, such as greater than two hours, preferably for about three or four hours or more.

It is preferable to include other ingredients in the formulation to enhance the efficacy of the antimicrobial composition. Included in this are essential oils to improve the rate at which the antimicrobial composition works as well as its residual activity. Suitable essential oils include Australian tea tree oil, lemongrass oil, thyme oil, lavender oil and clove oil and combinations thereof. Essential oils are used to increase the emolliency, moisturization, emollient and penetration properties of the present invention. Typically these oils are incorporated at the level of from about 1 to about 10 weighgt percent, and most preferably at about 5 weight percent based upon the total composition.

The present invention also employs thickening agents of acrylic acid which are crosslinked with an unsaturated polyfunctional agent such as polyallyl ether of sucrose. These acrylic acid functionalized polymers, commonly known as carbomers, are disclosed in U.S. Pat. Nos. 2,798,053 and 3,133,865 herein incorporated by reference.

The selection of the proper carbomer provides the antimicrobial formulation with the desired viscosity values. In order to have the desired feel the viscosity of the formulation must have a value of greater than about 5,000 centipoise. More preferably the formulations will have a viscosity of from about 9,000 to about 22,000 and most preferably from about 11,000 to about 20,000 centipoise as measured at 25° C.

A thickening agent, which is an addition agent comprised of an acrylic acid polymer crosslinked with an unsaturated polyallyl ether of sucrose is employed. The polymers are used in an amount sufficient to obtain a gelled composition of viscosity in the desired range.

A number of these polymers, known in the art as carbomers are commercially marketed by B.F. Goodrich, (Cleveland, Ohio) such as CARBOPOL® 934, 940 and 941; and by R.I.T.A. (Crystal Lake, Ill.) as ACRITAMER® 934,940 and 941, respectively. Typically the carbomer compounds are used from about 0.2 to about 2.0 percent by weight, and are preferably employed at a level of from about 0.4 to about 0.7 by weight of the total antimicrobial composition.

A preferred carbomer polymer, among several preferred carbomers is R.I.T.A. ACRITAMER® 505E, a polyvinyl carboxy polymer crosslinked with ethers of pentaerythritol. ACRITAMER® 505E is preferred as a gelling agent or viscosity enhancer because it provides a transparent or translucent gel in the present invention.

The most preferred carbomer is ULTREZ® 10 (available from BF Goodrich) a modified copolymer having a major portion of a monoolefinically unsaturated carboxylic acid monomer or its anhydride of 3 to 6 carbon atoms and a minor portion of a long chain acrylate or methacrylte ester monomer. The polymer is predominately acrylic acid and a smaller amount of a long chain acrylate monomer. The polymer is described in U.S. Pat. No. 5,004,598, hereby incorporated by reference in its entirety.

Another particularly preferred group of ingredients in the present invention are tack modifiers such as silicone waxes, stearoxy trimethyl silane, cyclomethicone, cetyl lactate, and alkyl lactates, (typically lengths $C_{12}$–$C_{15}$). Moisturizers such as glycerin, water, lipids, waxes and the like are also helpful when employed in the present invention. Other solvents are also employed, such as propylene glycol, in order to provide for a more stable formulation.

Other ingredients which may be added to the compositions include fragrances, emollients, pH adjusters, viscosity modifiers such as acrylic polymers, gums, xanthan gums and the like; transdermal enhancers, surfactants, dyes, colors and the like. These ingredients are well known in the art and are disclosed for example in U.S. Pat. No. 5,403,864 and 5,403,587. The remainder of the present formulation is made up of water, preferably deionized water. Water typically makes up from 10 to about 40% by weight of the antimicrobial composition.

The following formulation possesses highly effective antimicrobial properties.

1. Ethyl alcohol (40–70%), Isopropyl alcohol (20–25%), n-Propyl alcohol (5–10%)

2. Diisobutyl Phenoxy Ethoxy Ethyl Dimethyl Benzyl Ammonium chloride (0.05–0.5%), commonly known as benzethonium chloride
3. triclosan, commonly known as, 2, 4, 4'-trichloro-2-hydoxydiphenyl ether (0.2–0.5%)
4. N, N-Bis (Hydroxymethyl) urea (0.08–0.5%), Methyl p-Hydroxybenzoate (0.009–0.5%), Propyl p-Hydroxy benzoate (0.0025–0.5%), 1, 2-Propane diol (0.050–0.056%),
5. Coco Phosphotidyl PG-Dimonium chloride (0.05–0.5%)
6. DL- and L-Ofloxacin (0.01–0.5%)
7. Australian Tea Tree oil (1.0–5.0%)
8. Lemongrass oil (1.0–5.0%)
9. Thyme oil (1.0–5.0%)
10. Lavender oil (1.0–5.0%)
11. Clove oil (1.0–5.0%)

The antimicrobial compositions of the present invention are effective in controlling microorganisms when an effective amount of the composition is topically applied to a substrate or location, such as the hands, acne sites, or injection site for catheters, etc. The amount applied to be effective depends upon such environmental factors as the length of application, the amount of contact of the antimicrobial composition and the substrate, as well temperature and evaporation rates. Those with skill in the art will readily be able to determine the effective level necessary to control the microorganisms. Typically, from about 0.5 to about 10 milliliters, preferably from about 1.0 to about 8, and most preferably from about 2.5 to about 5 milliliters of the antimicrobial composition is applied. This amount of the antimicrobial composition is found to be effective, to provide a $\log_{10}$ reduction of 2 or more in the microbe population.

The present invention can also be prepared as an emulsion using techniques well known in the art, see for example U.S. Pat. No. 5,308,890. The active ingredients, excipients, ect., may be emulsified with an anionic, cationic, or nonionic surfactant or dispersing agent, or compatible mixtures thereof such as a mixture of an anionic or a nonionic surfactant, using, for example, from about 0.05% to about 5% by weight of a surfactant or dispersing agent based on the weight of the ingredients to be emulsified. Suitable cationic dispersion agents include lauryl pyridinium chloride, cetyldimethyl amine acetate, and alkyldimethylbenzylammonium chloride, in which the alkyl group has from 8 to 18 carbon atoms. Suitable anionic dispersing agents include, for example, alkali fatty alcohol sulfates, such as sodium lauryl sulfate, and the like; arylalkyl sulfonates, and the like; alkali alkyl sulfosuccinates, such as sodium octyl sulfosuccinate, and the like; and alkali arylalkylpolyethoxyethanol sulfates or sulfonates, such as sodium octylphenoxypolyethoxyethyl sulfate, having 1 to 5 oxyethylene units, and the like. Suitable non-ionic dispersing agents include, for example, alkyl phenoxypolyethoxy ethanols having alkyl groups from about 7 to 18 carbon atoms and from about 6 to about 60 oxyethylene units such as, for example, heptyl phenoxypolyethoxyethanols, ethylene oxide derivatives of long chained carboxylic acids such as lauric acid, myristic acid, palmitic acid, oleic acid, and the like, or mixtures of acids such as those found in tall oil containing from about 6 to 60 oxyethylene units; ethylene oxide condensates of long chained alcohols such as octyl, decyl, lauryl, or cetyl alcohols containing from 6 to 60 oxyethylene units; ethylene oxide condensates of long-chain or branched chain amines such as dodecyl amine, hexadecyl amine, and octadecyl amine, containing from about 6 to 60 oxyethylene units; and block copolymers of ethylene oxide sections combined with one or more hydrophobic propylene oxide sections. High molecular weight polymers such as hydroxyethyl cellulose, methyl cellulose, polyacrylic acid, polyvinyl alcohol, and the like, may be used as emulsion stabilizers and protective colloids.

The following examples are illustrative of the present invention and are not intended to limit the invention to the following compositions. Unless noted to the contrary, all percentages presented in this application are understood to be weight percent.

The following compositions were used in this application:

AMP 95 is a mixture of 2-amino-2-methyl-1-propanol, 2-(methylamino)-2-methyl-1-propanol and water in a ratio of from about 90:5:5, commercially available from Angus Chemical Company.

ACRITAMER® 505E, a polyvinyl carboxy polymer crosslinked with ethers of pentaerythritol, R.I.T.A.available from Crystal Lake, Ill.

ESS 9090IC is a fragrance, available from Givudan-Roure Corporation

CERAPHYL 28 is primarily cetyl lactate, a waxy solid commmercially available from ISP Van Dyk Inc.

CERAPHYL 41 is a mixture of $C_{12}$–$C_{15}$ alcohol lactates, available from ISP Van Dyk Inc.

DOW CORNING® 580 wax is a mixture of stearoxy trimethoxy silane and stearyl alcohol.

GERMABEN II is a mixture comprised of diazolindinyl urea (about 30%); methyl paraben (about 11%); propyl paraben (about 3%) and propylene glycol (about 56%), available from Sutton Laboratories.

GERMALL PLUS is a mixture of diazolidinyl urea (about 99%), 3-Iodo-propynylbutylcarbamate available from Sutton Laboratories.

LEXOREZ 100 is a saturated crosslinked hydroxy functional; polyester, comprised of glycerin, diethylene glycol, adipate crosslinked polymer, which is a viscous, hydrophobic liquid at room temperature and is dispersible in many lipids and emollients.

PHOSPOLIPID CDM is cocophosphatidyl (PG)-dimonium chloride,a co-synthetic, phospholipid available from Mona Industries, Inc.

PHOSPOLIPID PTC is cocamidopropyl phosphatidyl PG-dimonium chloride, available from Mona Industries.

SILSOFT PEDM phenylethyl dimethicone, available from Witco Corporation, Osi Specialties, Inc.

TRICLOSAN—2, 4, 4'-trichloro-2-hydoxydiphenyl ether.

ULTREZ® 10 a carbomer polymer, available from BF Goodrich, Cleveland Ohio, and disclosed in U.S. Pat. No. 5,004,598, the contents of which are incorporated by reference in its entirety.

EXAMPLE 1

The following formulations were prepared and tested, and the results are presented below:

Formulation 1: Ethyl alcohol 75.8; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245) 1.5; dimethicone (225) 0.5; Dow Corning 580 wax 0.20; SILSOFT PEDM 1.0; deionized water 17.6; PHOSPOLIPID CDM 0.2.

Formulation 2: Ethyl alcohol 50.0; Iso-propyl alcohol 20; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245)

1.0; dimethicone (225) 0.5; Dow Corning 580 wax 0.25; SILSOFT PEDM 1.0; deionized water 23.5; PHOSPOLIPID CDM 0.2.

Formulation 3: Ethyl alcohol 43.3; Iso-propyl alcohol 25; n-propyl alcohol 5.0; ULTREZ 10 0.6; glycerin 1.5; LEX-OREZ 100 0.25; CERAPHYL-41 0.5; CERAPHYL-28 0.5; triclosan 0.3; AMP pH 6.4; ESS 9090IC 0.06; cyclomethicone (245) 2.0; dimethicone (225) 0.5; Dow Corning 580 wax 0.1; SILSOFT PEDM 1.0; deionized water 19.0; PHOSPOLIPID CDM 0.2; Phenoxy ethanol 0.2.

Formulation 4: Ethyl alcohol 75.8; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245) 1.0; dimethicone (225) 0.5; Dow Corning 580 wax 0.25; SILSOFT PEDM 1.0; deionized water 17.5; PHOSPOLIPID CDM 0.2; GERMABEN-II 0.05; preservatives 0.15

Formulation 5: Ethyl alcohol 75.8; ULTREZ 10 0.6; glycerin 1.5; LEXOREZ 100 0.25; CERAPAYL-41 0.5; CERAPAYL-28 0.5; benzethonium chloride 0.2; AMP-95 pH 6.4; ESS 90901C 0.06; cyclomethicone (245) 1.0; dimethicone (225) 0.5; Dow Corning 580 wax 0.25; SILSOFT PEDM 1.0; deionized water 17.1; PHOSPOLIPID CDM 0.2.

Formulation 6: Ethyl alcohol 50; iso-propyl alcohol 20; ULTREZ 10 0.6; glycerin 1.5; LEXOREZ 100 0.25; CERAPAYL-41 0.5; CERAPAYL-28 0.5; 2, 4, 4-trichloro-2-hydroxydiphenyl ether 0.3; AMP-95 pH 6.4; ESS 9090IC 0.06; cyclomethicone (245) 1; dimethicone (225) 0.5; Dow Corning 580 wax 0.25; SILSOFT® PEDM 1.0; deionized water 23.0; PHOSPHOLIPID CDM 0.2; GERMABEN II 0.2; Disodium ethylenediaminetetraacetic acid (EDTA) 0.1.

Formulation 7: Ethyl alcohol 75.8; ULTREZ 10 0.6; glycerin 1.5; CERAPAYL-41 0.5; CERAPAYL-28 0.5; AMP-95 pH 6.4; ESS 9090IC 0.06; cyclomethicone (Dow Corning 245 fluid) 1.5; dimethicone (Dow Corning 225 fluid) 0.5; Dow Corning 580 wax 0.1; SILSOFT® PEDM 1.0; ; 2,4,4'-trichloro-2-hydroxydiphenyl ether 0.3; DL-Ofloxacin 0.05; deionized water 17.4.

Formulation 8: Ethyl alcohol 75.8; ULTREZ 10 0.6; glycerin 1.5; LEXOREZ 100 0.25; CERAPAYL-41 0.5; CERAPAYL-28 0.5; AMP-95 pH 6.4; ESS 9090IC 0.06; cyclomethicone (245) 1.5; dimethicone (Dow Corning 225) 0.5; Dow Corning 580 wax 0.1; SILSOFT PEDM 1.0; DL-Ofloxacin 0.25; deionized water 17.4.

Formulation 9: Ethyl alcohol 75.8; glycerin 1; 2, 4, 4'-trichloro-2-hydoxydiphenyl ether 0.3; ESS 9090IC 0.06; Tri-ethanolamine, (pH aduster), dimethicone (225) 1.0; Australian tea tree oil 1.5; deionized water 19.4; ACRITAMER 505E 0.45; PEG-75 Lanolin 0.5; Lavender oil 1.5.

Formulation 10: Ethyl alcohol 75.8; glycerin 1; 2, 4, 4'-trichloro-2-hydoxydiphenyl ether 0.3; ESS 9090IC 0.06; Triethanolamine (pH aduster), dimethicone (225) 1; deionized water 19.4; ACRITAMER 505E 0.45; PEG-75 Lanolin 0.5; Lavender oil 1.5.

Formulation 11: Ethyl alcohol 75.8; glycerin 1; 2, 4, 4'-trichloro-2-hydoxydiphenyl ether 0.3; ESS 9090IC 0.06; Triethanolamine (pH aduster), dimethicone (225) 1; deionized water 19.4; ACRITAMER 505E 0.45; PEG-75 Lanolin 0.5; Lemon Grass Oil 1.0.

Formulation 12: Ethyl alcohol 75.8; glycerin 1; 2, 4, 4'-trichloro-2-hydoxydiphenyl ether 0.3; ESS 9090IC 0.06; Triethanolamine (pH aduster), dimethicone (225) 1; deionized water 19.4; ACRITAMER 505E 0.45; PEG-75 Lanolin 0.5; Thyme Oil 1.0.

Formulation 13: Ethyl alcohol 75.8; glycerin 1; 2, 4, 4'-trichloro-2-hydoxydiphenyl ether 0.3; ESS 9090IC 0.06; Triethanolamine (pH aduster), dimethicone (225) 1; deionized water 19.4; ACRITAMER 505E 0.45; PEG-75 Lanolin 0.5; Clove Oil 1.0.

The antimicrobial formulations were evaluated for their ex-vivo clinical efficacy, and the test results of the compositions are summarized in Tables 1, 2 and 3.

A pig skin test model was used as a protocol to evaluate or screen a number of sample antimicrobial compositions. Because pig skin is similar to human skin in terms of skin components and behavior, pig skin is suitable to simulate hand washing techniques that are clinically performed by humans. The test is modeled after the test outlined in Pig Skin as Test Substrate for Evaluating Topical Antimicrobial Activity, J. Clin. Microbiology, September, 1986, p.343–348.

The pig skin test consisted of: a) preparation of the pig skin; b) antimicrobial challenge; and c) enumeration with controls.

The pig hide was washed and dehaired and then frozen. The pieces are then thawed and cut into 3×3 cm sections. The skin was mounted to a holder with an epoxy with the skin side exposed. The skin pieces were place into Petri dishes containing a filter disk moistened with 1.0 ml of water to prevent drying. The skins were placed in a refrigerator overnight.

On the same day that the skin was prepared, the test organism was innoculated on standard methods agar slants and standard methods agar plates in duplicate. The sectioned pig skin was tested for the presence of residual antibiotics by randomly cutting plugs (8 mm biopsy plug) from the hide and placing the plug skin side down into individual agar plates seeded with the test organism. On the following day, plates were examined for a zone inhibition surrounding the pig skin. An inhibition zone is indicative of residual antibiotics and the skin was not used.

Suspensions of the various organisms were made from overnight slant cultures. Cultures were suspended with 10 ml of Butterfield buffer by gently rubbing the surface with agar with a sterile cotton swab. The suspensions were mixed together to provide a mixed innoculum of approximately $10^9$ CFU/ml. The titer of organisms was further diluted to yield approximately $10^7$ CFU/ml. Two pieces of pig skin were innoculated with 0.05 ml of diluted culture. Each pair of innoculated skin was paired with an uninnoculated skin. The pair inoculated and uninnoculated skin were rubbed together for approximately 15 seconds and incubated for approximately 15 minutes at 30° C. with the cover removed to allow the organisms to dry onto the skin. After incubation 0.50 ml of test material was added to the pieces of skin from each pair. Incubation was done at room temperature with the Petri dish cover removed. One paired duplicate from each set was enumerated through imprinting onto an agar plate while the other duplicate was enumerated by rinsing.

Imprints were made by inverting the mounting holder and pressing the treated skin onto the surface of standard methods agar with lecithin and polysorbate 80. Imprints were made at specified time intervals and then incubated at approximately 30° C. for about 24 hours.

At each time interval, 0.2 ml of letheen thioglycolate neutralizing broth was added to the surface of the pair of skin from the pair. The resulting 10 ml wash from using both pieces of skin was collected and used to enumerate the surviving organisms. Aliquots (0.5 ml) of wash broth were serially diluted to extinction in 4.5 ml of letheen thioglycolate neutralizing broth. Plates were incubated at 30° C. for approximately 48 hours and then counted.

The results are presented below:

TABLE 1

Pig Skin test results with a Mixed Culture*

| Formula-<br>tion | Inoculum<br>Controls<br>(BL)<br>($Log_{10}$) | $Log_{10}$ Reductions | | |
|---|---|---|---|---|
| | | 15 min. | 60 min. | 120 min. |
| 1 | 7.42 | 1.8 | 2.48 | 1.85 |
| 2 | 5.84 | 1.1 | 2.7 | 2.38 |
| 3 | 7.24 | 1.7 | 2.65 | 0.83 |
| 4 | 7.42 | 1.78 | 1.76 | 3.76 |
| 5 | 5.84 | 4.1 | 2.8 | 2.17 |
| 6 | 5.84 | 3.55 | 2.65 | 2.10 |
| 7 | 5.84 | 3.82 | 3.38 | 3.61 |
| 8 | 5.84 | 4.14 | 3.94 | 4.44 |
| HIBISTAT | 5.84 | 3.0 | 3.3 | 0.62 |

*Mixed Culture with each of the cultured materials equally
represented:  Pseudomonas aeruginosa   ATCC 15442,
              Klebseila pneuinoniae    ATCC 11296,
              Micrococcus luteus       ATCC 7468,
              Enterococcus faecalis    ATCC 29212

Those with skill in the art will appreciate that the compositions with higher $log_{10}$ reduction value indicates improved efficacy. The $log_{10}$ reduction is the difference in the initial bacterial counts and the count recovered after each treatment.

The same formulations were tested on Pig Skin test results on *Staphylococcus aureus* ATCC 33592. The results, reported with time reported in minutes, are presented in Table 2 below:

TABLE 2

| Formula-<br>tion | Inoculum<br>Controls<br>(BL)<br>($Log_{10}$) | $Log_{10}$ Reductions | | |
|---|---|---|---|---|
| | | 15 min. | 60 min. | 120 min. |
| 1 | 7.55 | 2.28 | 2.06 | 1.98 |
| 2 | 4.99 | 1.37 | 1.88 | 0.03 |
| 3 | 7.55 | 2.45 | 3.04 | 2.54 |
| 4 | 7.55 | 4.2 | 2.22 | 1.8 |
| 5 | 4.99 | 1.74 | 1.96 | 2.19 |
| 6 | 4.99 | 0.15 | 2.23 | 2.18 |
| 7 | 4.99 | 2.58 | 2.83 | 3.14 |
| 8 | 4.99 | 2.84 | 2.65 | 2.86 |
| HIBISTAT | 4.99 | 2.45 | 1.54 | 0.85 |

The results in Table 2 indicate that excellent bactericidal activity was obtained against Staphylococcus aureus using the iso-propyl alcohol formulations.

The same formulations were tested using Pig Skin test protocol on *Serratia marcescens* ATCC 14756. The results are presented in Table 3 below:

TABLE 3

| Formula-<br>tion | Inoculum<br>Controls<br>(BL)<br>($Log_{10}$) | $Log_{10}$ Reductions | | |
|---|---|---|---|---|
| | | 15 min. | 60 min. | 120 min. |
| 1 | 7.01 | 1.93 | 1.25 | 1.04 |
| 2 | 5.17 | 2.32 | 0.96 | 0.4 |
| 3 | 7.01 | 2.1 | 1.77 | 1.10 |
| 4 | 7.01 | 3.53 | 3.07 | 0.77 |
| 5 | 5.17 | 2.64 | 1.64 | 1.48 |
| 6 | 5.17 | 3.32 | 2.18 | 0.32 |
| 7 | 5.17 | 2.18 | 3.29 | 2.26 |
| 8 | 5.17 | 3.52 | 2.9 | 1.63 |
| 9 | 7.04 | 2.12 | 3.08 | 2.78 |
| 10 | 7.04 | 4.52 | 3.51 | 2.96 |
| 11 | 7.04 | 3.76 | 3.89 | 2.89 |
| 12 | 7.04 | 3.23 | 3.36 | 3.31 |
| 13 | 7.04 | 4.11 | 3.89 | 1.93 |
| HIBISTAT | 5.17 | 2.08 | 2.06 | 0.03 |

Table 3 indicates that ethyl alcohol and isopropyl alcohol antimicrobial formulations containing essential oils, particularly Lemongrass oil, Lavender, Thyme, Australian tea tree oil and clove oil provided excellent activity against Serratia marcescens ATCC 14756.

EXAMPLE 2

Based upon the results found in Example 1 above, four formulations, (A–D) were prepared and were evaluated for their in-vivo efficacy following a modified Health Care Personnel Handwash protocol. The four formulations are as follows:

Formulation A: Ethyl alcohol (92.3% by weight) 75.8; ULTREZ® 10 0.6; glycerin 0.5; LEXOREZ® 100 0.25; CERAPHYL-41 0.5; CERAPHYL-28 0.5; triclosan (2, 4, 4-trichloro-2-hydoxydiphenyl ether) 0.3; phenoxy ethanol 0.3; benzalkonium chloride (50% solution) 0.2; PHOSPHOLIPID CDM 0.05; GERMALL PLUS+ GERMABEN II (1:1 weight ratio) 0.2; Vitamin E linoleate 0.05; AMP pH 6.4; ESS 9090IC 0.06; deionized water 20.4.

Formulation B: Formulation B is substantially similar to Formulation A except no triclosan was employed. Ethyl alcohol 75.8; ULTREZ® 10 0.6; glycerin 0.5; LEXOREZ® 100 0.25; CERAPHYL-41 0.5; CERAPHYL-28 0.5; phenoxy ethanol 0.3; benzalkonium chloride (50% solution) 0.2; PHOSPHOLIPID CDM 0.05; GERMALL PLUS+ GERMABEN (1:1) 0.2; Vitamin E linoleate 0.05; AMP pH 6.4; ESS 9090IC 0.06; deionized water 20.5.

Formulation C: Ethyl alcohol 75.8; ULTREZ 10 0.6; glycerin 1.5; LEXOREZ 100 0.25; CERAPHYL 41 0.5; CERAPHYL 28 0.5; 2, 4,4'-trichloro-2-hydoxydiphenyl ether 0.3; phenoxyethanol 0.3; benzethonium chloride 0.1; benzalkonium chloride (50% solution) 0.1; PHOSPHOLIPID CDM 0.05; GERMALL PLUS+GERMABEN (1:1) 0.2; Vitamin E linoleate 0.05; AMP pH 6.4; ESS 90901C 0.06; cyclomethicone (245) 2.5; dimethicone (225) 0.5; Dow Corning 580 wax 0.1; SILSOFT PEDM 0.5; deionized water 15.8.

Formulation D: Ethyl alcohol 43.2; iso-propyl alcohol 25; n-propyl alcohol 5; ULTREZ 10 0.6; glycerin 1.5; LEXOREZ® 100 0.25; CERAPHYL-41 0.5; CERAPHYL-28 0.5; 2, 4, 4'-trichloro-2-hydoxydiphenyl ether 0.3; phenoxy ethanol 0.3; benzalkonium chloride (50% solution) 0.2; Vitamin E linoleate 0.025; AMP pH 6.4; ESS 9090IC 0.06; cyclomethicone (245) 3.5; dimethicone (225) 0.5; Dow Corning 580 wax 0.1; SILSOFT PEDM 0.5; lemon grass oil 2.5; Australian tea tree oil 2.5; deionized water 12.

These formulations were compared with commercially available chlorhexidine gluconate based products such as HIBISTAT and HIBICLENS, commercially available antimicrobials from ICI Americans.

TABLE 4

Log$_{10}$ Reductions from Baseline Using the Health Care Personnel Handwash Protocol

| Formulations | Base Line | Wash 1 | Wash 3 | Wash 7 | Wash 10 |
|---|---|---|---|---|---|
| A | 8.23 | 3.55 | 3.08 | 3.67 | 3.03 |
| B | 8.56 | 4.13 | 3.4 | 3.92 | 3.04 |
| C | 8.36 | 3.75 | 3.15 | 3.06 | 3.18 |
| D | 8.45 | 4.26 | 4.42 | 4.55 | 4.57 |
| HIBISTAT | 8.23 | 3.25 | 3.94 | 5.31 | 2.86 |
| HIBICLENS | 8.32 | 2.2 | 2.6 | 3.0 | 2.9 |

All four formulations from Example 1 met FDA requirements at wash 1, (a 2 log$_{10}$ reduction), and at wash 10, (a 3 log$_{10}$ reduction). Formulations A–D, were found to be more effective than the commercially available products. Alcohol and chlorhexidine gluconate combinations do show excellent build-up on 10 handwashes, but at the 10th wash, where a neutralizer is being used to quench the activity, a drop was noted in the log reduction value from the 7th wash ranging between 40 and 50%. surprisingly, all four formulations of the present invention did not replicate this drop in efficacy.

EXAMPLE 3

Additional experimental formulations were prepared as emulsions, using the antimicrobial formulations described in Examples 1 and 2 above, with minor modifications. In total 8 samples were prepared out of which four test formulations were evaluated using an in-vitro bactericidal test against 8 representative microorganisms (gram negative, gram positive and fungus) at four time intervals, and two concentrations.

The formulations used in this Example are set forth below:

Formulation A': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy timethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+ 0.8, Phenoxy Ethanol 0.4, Lactic Acid 0.5, GERMABEN-II 0.25, Panthenol 0.2, Tocopheryl Acetate 0.05, Vitamin E Linoleate 0.05, Tricoslan 0.3.

Formulation B': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy timethyl silane 1, Sorbitane Stearate 0.8, Cetyl Alcohol 0.5, Stearyl Alcohol 0.5, Synthetic Beeswax 0.5, Benzyl Alcohol 0.8, Carbomer 941 1.0, Fragrance IFF 1906AD 0.2, Disodium EDTA+NaOH 0.15+ 0.75, Phenoxy Ethanol 0.4, Lactic Acid 0.5, sodium hydroxy methyl glycinate (50% active) 0.3, GERMABEN-II 0.25, Benzethonium Chloride 0.2, Tocopheryl acetate 0.05, Vitamin E Linoleate 0.05, Phospholipid PTC+CDM (1:1) 1, Tricoslan 0.3, GS-Liquorice 0.1.

Formulation C': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy timethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+ 0.75, Phenoxy Ethanol 0.4, Lactic Acid 0.5, GERMALL Plus 0.3, GERMABEN-II 0.25, Benzalkonium Chloride (50%) 0.2, Tocopheryl acetate 0.05, Vitamin E Linoleate 0.05, Phospholipid PTC+CDM (1:1) 1, Tricoslan 0.3.

Formulation D': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy timethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+ 0.75, Phenoxy Ethanol 0.4, Lactic Acid 0.5, octanoyl collagenic acid 0.3, GERMABEN-II 0.25, Cetyl pyridinium chloride 0.2, Tocopheryl Acetate 0.05, Vitamin E Linoleate 0.05, PHOSPHOLIPID PTC+CDM (1:1) 1, Tricoslan 0.3.

TABLE 5

In-vitro bactericidal activity of emulsions

| | | Time* for >99.99% Kill | | | |
|---|---|---|---|---|---|
| Microorganism | ATCC | A' | B' | C' | D' |
| Enterococcus faecalis (MDR) | 51299 | 60 | 60 | 15 | 15 |
| Staphylococcus aureus (MRSA) | 33592 | 60 | 60 | 15 | 60 sec. |
| Staphylococcus aureus | 6538 | 60 | 60 | 15 | 15 |
| Serratia marcescens | 14756 | >60 | 60 | 15 | 60 sec. |
| Streptococcus pneumoniae | 6303 | 15 | 15 | 15 | 30 sec. |
| Escherichia coli | 11229 | 15 | 15 | 30 sec. | 30 sec. |
| Pseudomonas aeruginosa | 15442 | 30 sec. | 30 sec. | 30 sec. | 30 sec. |
| Candida albicans | 10231 | all results more than 60 | | | |

The above data indicates the superior efficacy that Formulation D' has in killing both the gram positive and gram negative bacteria indicated above.

The antimicrobial mixture of the present invention has shown comparable activity when formulated in non-aqueous base, i.e., when made into an emulsion. Formulation D' displayed promising results particularly against Staphylococcus aureus (MRSA) and Serratia marcescens (ATTC 14756). Most triclosan-containing antimicrobial formulations have limited activity against Serratia marcescens (ATTC 14756). The anticmocrobial compositions of the present invention, and in particular formulation D', have potential application in topical skin care products, like alcohol gels, creams, lotions, scrubs, pre-operative preparations, cleansers, ointments, therapeutics and other applications against disease causing pathogens.

EXAMPLE 4

Compositions of the present invention were tested for irritation and sensitivity. The following formulations were prepared:

Formulation 1 deionized water 28.7, ethyl alcohol 62, ULTREZ® 10 0.45, glycerin 0.5, cyclomethicone 1.25, Dow Corning® 580 Wax 0.025, SILSOFT® PEDM 0.2, CERAPHYL®-28 0.5, CERAPHYL®-41 1.0, AMP 95 (pH adjuster) as needed, 1906 AD MOD I 0.1.

Formulation 2 deionized water 27.7, ethyl alcohol 62, ULTREZ 10 0.55, glycerin 0.5, cyclomethicone 1.25, Dow Corning 580 Wax 0.025, SILSOFT® PEDM 0.2, CERAPHYL®-28 0.5, CERAPHYL®-41 1.0, AMP 95 (pH adjuster) as needed, 1906 AD MOD I 0.06, phenoxy ethanol 0.5, benzalkonium chloride (50% active) 0.16, benzethonium chloride 0.08, PHOSPHOLIPID CDM 0.05, GERMALL Plus 0.1, GERMABEN II 0.1.

Prior to study the subjects were screened to assure that they met the inclusion/exclusion criteria. Each subject was provided with a schedule of the study activities. The Induction Phase consisted of nine (9) consecutive applications of the study material and subsequent evaluations of the study sites were assessed. Prior to the applications of the patches, the sites were outlined with a skin marker, e.g., gentian violet. The subjects were required to remove the patches approximately 24 hours after application. The subjects returned to the facility at 48 hour intervals to have the sites evaluated and identical patches reapplied. Following the ninth evaluation, the subjects were dismissed for a 10–14 day rest period. After the rest period, the challenge period was initiated during the 6th week of the study with the identical patches applied to the sites previously unexposed to the study. These patches were removed by subjects after 24 hours and the sites graded after additional 24-hour and 48 hour periods. The gradings were done 48 and 72 hours after application. To be considered a completed case, a subject must have nine (9) applications and no less than eight (8) subsequent readings during induction and one (1) product application and two (2) readings during the challenge. Of the 101 subjects that completed the study, there was no evidence of sensitization or irritation due to the formulations.

EXAMPLE 6

The two formulations employed in Example 5 above were investigated to determine their moisturizing capabilities. Fifteen subjects applied the formulations to the dry skin on the lateral aspect of the lower leg. The moisturization of the skin was measured using the SKICON® Skin Surface Hydrometer. All results are reported as mean percent changes from baseline in SKICON measurements. As used herein mean percent results were found by compared by measuring the moisturization values at four diferent sites and comparing the mean value of moisturization for the four sites with baseline values.

|  | 30 Minutes | 1 Hour | 2 Hours |
|---|---|---|---|
| Formulation 1 | 4.6% | 16.7% | 19.9% |
| Formulation 2 | 5.5% | 18.8% | 23.3% |
| Untreated control | 16.5 | 35.3% | 39.7% |

The results indicated that both Formulations 1 and 2 behaved similarly when compared with the and were superior to the untreated control. This indicates that the formulations were non-drying. Both formulations were surprising in that for formulations containing high levels of alcohol the products were not found to posses significant drying effects.

EXAMPLE 7

The following product formulation was prepared and tested in order to evaluate the antimicrobial properties using different microbiological strains: deionized water 27.8; ethyl alcohol 62.0 by volume; ULTREZ 10 0.55; glycerin 0.5; cyclomethicone (245) 1.25; Dow Corning 580 wax 0.025; SILSOFT PEDM 0.2; CERAPHYL-28 0.5; CERAPHYL-41 1.0; phenoxy ethanol 0.5; benzalkonium chloride (50% active) 0.2; PHOSPHOLIPID CDM 0.05; GERMALL PLUS 0.1; GERMABEN II 0.1; 1906-AD Mod I 0.06 and pH adjuster.

The antimicrobial properties of the formulation was evaluated a concentration of 99%(w/v), using exposure of fifteen seconds, thirty seconds, and one minute. The samples were prepared using a 0.1 ml aliquot of challenge suspension of approximately $1.0 \times 10^9$ CFU/ml and were added to 9.9 ml of product and mixed thoroughly to achieve a 99% (w/v) concentration. The 15 second, 30 second and one minute exposures were timed with a calibrated minute/second timer.

0.1 ml of each challenge suspension was placed into a sterile test tube containing 9.9 ml of Butterfield's Phosphate Buffer solution. This solution was used as a control. Appropriate ten-fold dilutions were made with Butterfield's Phosphate Buffer solution. After incubation, approximately 1–2 days at 35° C., the colonies on the plates were counted using a hand-tally counter. The $\log_{10}$ values of the plates were compared to the initial population. It is understood that the numbers reported below as 10+7 is $10^7$. The results are as follows:

| Organism | Exp. Time | Inoculum Level LOG | Inoculum Level CFU/ml | Avg. Pop. After Exposure LOG | Avg. Pop. After Exposure CFU/ml | Log Reduction | % Reduction |
|---|---|---|---|---|---|---|---|
| B. cereus | 15 sec | 5.7118 | 5.150 × 10 + 5 | 1.0000 | 1.00 × 10 + 1 | 4.7118 | 99.9981% |
|  | 30 sec | 5.7118 | 5.150 × 10 + 5 | 1.0000 | 1.00 × 10 + 1 | 4.7118 | 99.9981% |
|  | 60 sec | 5.7118 | 5.150 × 10 + 5 | 1.0000 | 1.00 × 10 + 1 | 4.7118 | 99.9981% |
| B. subtilis | 15 sec | 5.4393 | 2.750 × 10 + 5 | 4.7364 | 5.450 × 10 + 4 | 0.7029 | 80.1818% |
|  | 30 sec | 5.4393 | 2.750 × 10 + 5 | 4.6902 | 4.90 × 10 + 4 | 0.7491 | 82.1818% |
|  | 60 sec | 5.4393 | 2.750 × 10 + 5 | 4.6857 | 4.850 × 10 + 4 | 0.7536 | 82.3636% |
| C. albicians | 15 sec | 7.3664 | 2.3250 × 10 + 7 | 1.000 | 1.00 × 10 + 1 | 6.3664 | 99.9999% |
|  | 30 sec | 7.3664 | 2.3250 × 10 + 7 | 1.0000 | 1.00 × 10 + 1 | 6.3664 | 99.9999% |
|  | 60 sec | 7.3664 | 2.3250 × 10 + 7 | 1.0000 | 1.00 × 10 + 1 | 6.3664 | 99.9999% |
| E. faecalis | 15 sec | 7.1847 | 1.530 × 10 + 7 | 1.3979 | 2.50 × 10 + 1 | 5.7868 | 99.9999% |
|  | 30 sec | 7.1847 | 1.530 × 10 + 7 | 1.0000 | 1.00 × 10 + 1 | 6.1847 | 99.9999% |
|  | 60 sec | 7.1847 | 1.530 × 10 + 7 | 1.0000 | 1.00 × 10 + 1 | 6.1847 | 99.9999% |
| E. coli | 15 sec | 7.3608 | 2.2950 × 10 + 7 | 1.0000 | 1.00 × 10 + 1 | 6.3608 | 99.9999% |
|  | 30 sec | 7.3608 | 2.2950 × 10 + 7 | 1.0000 | 1.00 × 10 + 1 | 6.3608 | 99.9999% |
|  | 60 sec | 7.3608 | 2.2950 × 10 + 7 | 1.0000 | 1.00 × 10 + 1 | 6.3608 | 99.9999% |

-continued

| Organism | Exp. Time | Inoculum Level LOG | Inoculum Level CFU/ml | Avg. Pop. After Exposure LOG | Avg. Pop. After Exposure CFU/ml | Log Reduction | % Reduction |
|---|---|---|---|---|---|---|---|
| P. aeruginosa | 15 sec | 7.0864 | 1.220 × 10 + 7 | 1.0000 | 1.00 × 10 + 1 | 6.0864 | 99.9999% |
| | 30 sec | 7.0864 | 1.220 × 10 + 7 | 1.0000 | 1.00 × 10 + 1 | 6.0864 | 99.9999% |
| | 60 sec | 7.0864 | 1.220 × 10 + 7 | 1.0000 | 1.00 × 10 + 1 | 6.0864 | 99.9999% |
| S. typhimurium | 15 sec | 6.8028 | 6.350 × 10 + 6 | 1.0000 | 1.00 × 10 + 1 | 5.8028 | 99.9999% |
| | 30 sec | 6.8028 | 6.350 × 10 + 6 | 1.0000 | 1.00 × 10 + 1 | 5.8028 | 99.9999% |
| | 60 sec | 6.8028 | 6.350 × 10 + 6 | 1.0000 | 1.00 × 10 + 1 | 5.8028 | 99.9999% |
| S. marcescens | 15 sec | 7.356 | 2.270 × 10 + 7 | 1.0000 | 1.00 × 10 + 1 | 6.3560 | 99.9999% |
| | 30 sec | 7.356 | 2.270 × 10 + 7 | 1.0000 | 1.00 × 10 + 1 | 6.3560 | 99.9999% |
| | 60 sec | 7.356 | 2.270 × 10 + 7 | 1.0000 | 1.00 × 10 + 1 | 6.3560 | 99.9999% |

The formulation demonstrates excellent antimicrobial activity, 99% reduction against all of the listed organisms. The above organisms include a broad spectrum of organisms, including gram negative, gram positive, and fungi microbes.

EXAMPLE 8

Subjects were instructed not to use any anti-microbial and or antiseptic articles, with the exception of the test articles. Petri dishes were filled with approximately 11.5 ml of sterilized molten soybean casein digest agar. The agar was allowed to solidify and was placed in an incubator at 35° C. overnight prior to innoculation. The test bacteria were grown in trypticase soy broth and diluted to obtain approximately 200–300 colony forming units (CFU) per 10 microliters. A 10 microliter loop was used to deliver 10 microliter of the final dilution onto the covered surface of each agar plate and spread using the loop. The plates were allowed to dry inside the Petri dishes for 15–30 minutes before application to the subject arms. Prior to application to the subject's arms 70% iso-propyl alcohol was used for about 10 seconds to reduce the possibility of contamination. A technician applied about 2.5 ml of the test solution over the volar surface of the subject's arm. The subject then spread the solution from wrist to elbow until the test article disappeared.

After applying and air drying, the subjects were challenged with the anti-microbial solution either immediately (within 5 minutes of treatment), 1 hour, 3 hours 5 or 8 hours post treatment. The antimicrobial solutions used were a commercially available 62% by volume ethyl alcohol (designated as A) and the formulation used in Example 7 above (designated as B). The results were as follows:

| Treatment:Time of Exposure | Untreated Sites* | Treated Sites* |
|---|---|---|
| B - 8 Hours | 77 | 83 |
| | 118 | 125 |
| | 64 | 71 |
| | 103 | 115 |
| | 88 | 111 |
| | 107 | 97 |
| Average for Group B - 5 hours | 92.8 | 100 |
| | 124 | 125 |
| | 84 | 83 |
| | 135 | 89 |
| | 67 | 93 |
| | 87 | 21 |
| | 134 | 40 |
| Average for Group | 105 | 76 |

-continued

| Treatment:Time of Exposure | Untreated Sites* | Treated Sites* |
|---|---|---|
| B - 3 hours | 132 | 6 |
| | 87 | 0 |
| | 127 | 3 |
| | 107 | 10 |
| | 153 | 86 |
| | 113 | 48 |
| Average for Group B - 1 hour | 120 | 26 |
| | 79 | 63 |
| | 100 | 5 |
| | 68 | 81 |
| | 71 | 2 |
| | 127 | 10 |
| | 118 | 0 |
| Average for Group A - 1 hour | 94 | 27 |
| | 139 | 169 |
| | 130 | 136 |
| | 121 | 164 |
| | 137 | 167 |
| | 98 | 135 |
| | 99 | 117 |
| Average for Group B - 5 minutes | 121 | 148 |
| | 91 | 0 |
| | 142 | 1 |
| | 116 | 2 |
| | 86 | 0 |
| | 95 | 0 |
| | 91 | 0 |
| Average for Group | 104 | 0.5 |

*Colony Forming Units (CFU)

The above data indicates that the present invention was very effective in killing germs at 5 minutes and also had very effective residual activity after 3 hours in preventing microbial growth.

We claim:

1. An antimicrobial composition comprising:
   a) from about 55 to about 90 percent by volume alcohol;
   b) an effective amount of an antimicrobial material selected from the group consisting of phenoxy ethanol, benzalkonium chloride, benzethonium chloride, cocophosphatidyl-dimonium chloride and mixtures thereof;
   c) a thickener consisting of from about 0.4 to about 0.7 weight percent of a carbomer polymer which is a copolymer having a major portion comprising a monoolefinically unsaturated carboxylic acid monomer or its anhydride of 3 to 6 carbon atoms; and a minor portion of a long chain acrylate or methacrylate ester monomer; said antimicrobial composition having a viscosity of from about 9,000 to about 22,000 centipoise as measured at 25° C.

2. The composition of claim 1 wherein the alcohol is selected from the group consisting of ethyl alcohol, isopropyl alcohol, n-propyl alcohol and mixtures thereof.

3. The composition of claim 1 wherein phenoxy ethanol is present in amount from about 0.25 to about 5.0 percent by weight; benazalkonium chloride is present in the amount from about 0.02 to about 1.0 percent by weight; and cocophosphatidyl-dimonium chloride is present in the amount from about 0.01 to about 1.0 percent by weight.

4. The composition of claim 1 which additionally contains an effective amount of diazolidinyl urea and 3-Iodo-propynylbutylcarbamate.

5. The composition of claim 4 wherein the total amount of diazolidinyl urea and 3-Iodo-propynylbutylcarbamate is from about 0.05 to about 0.5 percent by weight.

6. The composition of claim 4 which additionally contains an effective amount of methyl paraben; propyl paraben; and propylene glycol.

7. The composition of claim 6 wherein the total amount of diazolindinyl urea; methyl paraben; propyl paraben; and propylene glycol is from about 0.05 to about 0.5 percent by weight.

8. The composition of claim 1 which additionally contains an effective amount of cocamidopropyl phosphatidyl dimonium chloride.

9. The composition of claim 8 wherein the amount of cocamidopropyl phosphatidyl dimonium chloride is from about 0.01 to about 1.0 percent by weight.

10. A method of disinfecting a substrate comprising applying an effective amount of the antimicrobial composition of claim 1 to a substrate.

11. The method of claim 10 wherein the substrate is the hand.

12. A method for controlling *Staphylococcus aureaus* (MRSA) comprising topical administration to a substrate an anti-microbially effective amount of the composition of claim 1.

13. A method for controlling *Staphylococcus aureaus* (MRSA) comprising topical administration to a substrate an anti-microbially effective amount of the composition according to claim 2.

14. A method for controlling Serratia marcescens ATCC 14756 comprising topical administration to a substrate an anti-microbially effective amount of the composition of claim 1.

15. A method for providing moisture to the skin comprising the application of an effective amount of the composition of claim 1 to the skin.

16. The method of claim 15 wherein the amount of composition applied to the skin is from about 0.5 to about 10 milliliters.

17. The composition of claim 1 which additionally contains an effective amount of an essential oil selected from the group consisting of Australian tea tree oil, lemongrass oil, thyme oil, lavender oil, and clove oil.

18. The composition of claim 2 which additionally contains an effective amount of an essential oil selected from the group consisting of Australian tea tree oil, lemongrass oil, thyme oil, lavender oil, and clove oil.

19. The composition of claim 1 which additionally contains an effective amount of octanoyl collagenic acid and cetyl pyridium chloride.

20. An antimicrobial composition consisting essentially of:
   a) from about 55 to about 90 percent by volume alcohol;
   b) an effective amount of an antimicrobial material selected from the group consisting of phenoxy ethanol, benzalkonium chloride, benzethonium chloride and cocophosphatidyl-dimonium chloride;
   c) from about 0.4 to about 0.7 weight percent of a carbomer polymer, the carbomer polymer is a copolymer having a major portion comprising a monoolefinically unsaturated carboxylic acid monomer or its anhydride of 3 to 6 carbon atoms; and a minor portion of a long chain acrylate or methacrylate ester monomer; said antimicrobial composition having a viscosity of from about 9,000 to about 22,000 centipoise as measured at 25° C.

* * * * *